United States Patent
Rothkopf et al.

(10) Patent No.: US 12,082,858 B2
(45) Date of Patent: Sep. 10, 2024

(54) BONE FIXATION SYSTEM

(71) Applicant: B-Plate Inc., Chesterland, OH (US)

(72) Inventors: F. David Rothkopf, Ashland, MA (US); Joseph Traut, Sharon, MA (US); Tom Beltavski, Broadview Heights, OH (US); Jason Gromek, Brecksville, OH (US)

(73) Assignee: B-Plate Inc., Chesterland, OH (US)

( * ) Notice: Subject to any disclaimer, the term of this patent is extended or adjusted under 35 U.S.C. 154(b) by 0 days.

(21) Appl. No.: 18/388,663

(22) Filed: Nov. 10, 2023

(65) Prior Publication Data

US 2024/0074802 A1 Mar. 7, 2024

Related U.S. Application Data

(63) Continuation of application No. PCT/US2022/029159, filed on May 13, 2022.

(60) Provisional application No. 63/188,492, filed on May 14, 2021.

(51) Int. Cl.
| | | |
|---|---|---|
| *A61B 17/80* | (2006.01) | |
| *A61B 17/00* | (2006.01) | |
| *A61B 17/56* | (2006.01) | |

(52) U.S. Cl.
CPC ...... *A61B 17/8047* (2013.01); *A61B 17/8057* (2013.01); *A61B 2017/00946* (2013.01); *A61B 2017/564* (2013.01)

(58) Field of Classification Search
CPC .................................................. A61B 17/8047
See application file for complete search history.

(56) References Cited

U.S. PATENT DOCUMENTS

| | | |
|---|---|---|
| 6,287,309 B1 | 9/2001 | Baccelli et al. |
| 7,491,221 B2 | 2/2009 | David |
| 8,992,581 B2 | 3/2015 | Austin et al. |
| 9,072,555 B2 | 7/2015 | Michel |
| 9,861,405 B2 | 1/2018 | Day et al. |
| 10,849,668 B2 | 12/2020 | Globerman et al. |
| 2013/0131732 A1* | 5/2013 | Harris ............... A61B 17/8695 606/279 |
| 2013/0184765 A1* | 7/2013 | Beyar ............... A61B 17/8057 606/305 |

(Continued)

FOREIGN PATENT DOCUMENTS

EP 0637437 A1 2/1995

OTHER PUBLICATIONS

International Search Report and Written Opinion in International Application No. PCT/US2022/029159, mailed Aug. 3, 2022, 8 pages.

*Primary Examiner* — Olivia C Chang
(74) *Attorney, Agent, or Firm* — Kintner IP, LLC; Mary Frances Ludwig

(57) ABSTRACT

A bone fixation system includes a fixation plate formed of a fiber reinforced polymer composite material with a plurality of apertures configured to receive screws for fracture fixation. An malleable metallic insert is disposed within each aperture. The inserts may be sized to accept locking or non-locking screws over a range of angles. The inserts may protrude through the plate on the bone side, providing clearance between the composite plate and the bone. The apertures and inserts may have a generally cylindrical or obround shape. In embodiments, the inserts are shaped complementary to the apertures in which they are disposed.

12 Claims, 7 Drawing Sheets

(56) References Cited

U.S. PATENT DOCUMENTS

2019/0029739 A1\* 1/2019 Finley ................ A61B 17/8061
2020/0155209 A1\* 5/2020 Bottlang .............. A61B 17/863
2021/0106367 A1 4/2021 Leak \* cited by examiner

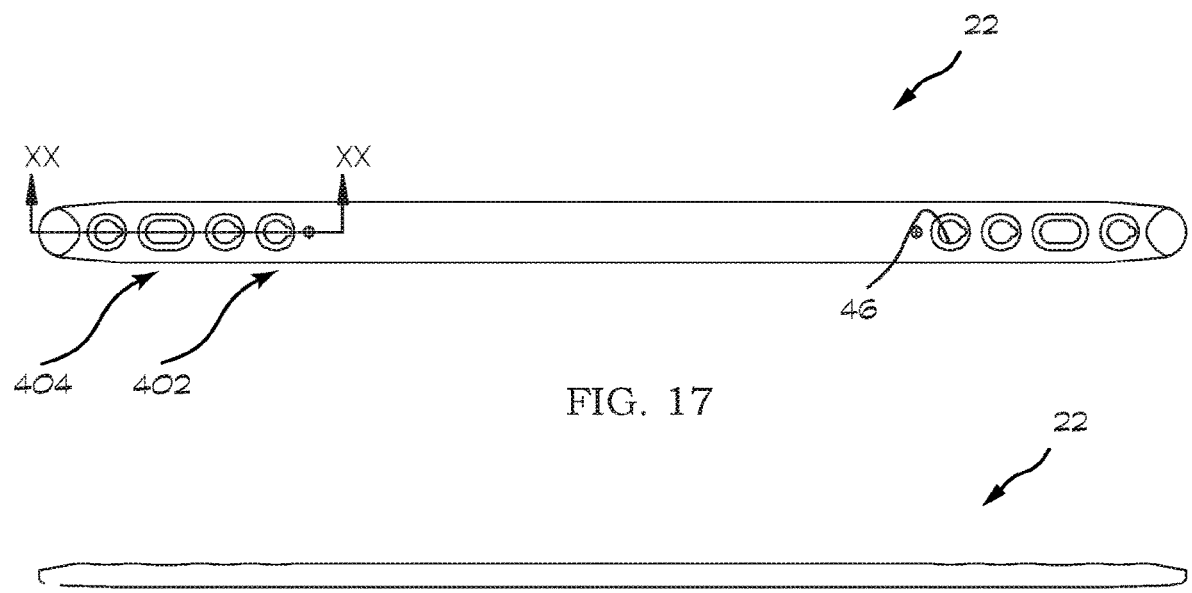
FIG. 17
FIG. 18
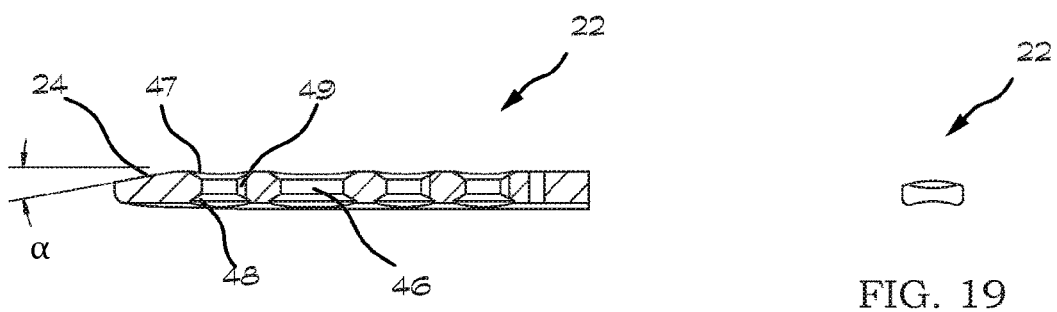
FIG. 19
FIG. 20

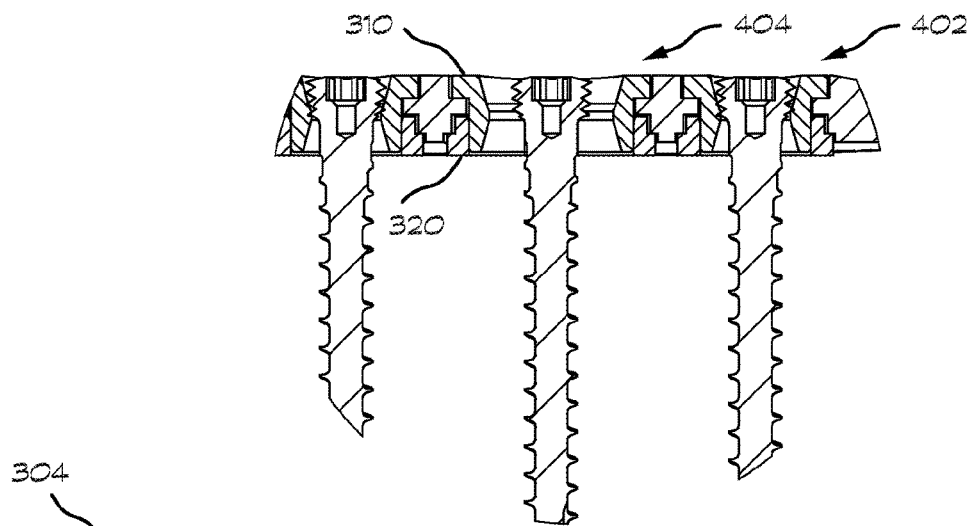
FIG. 23
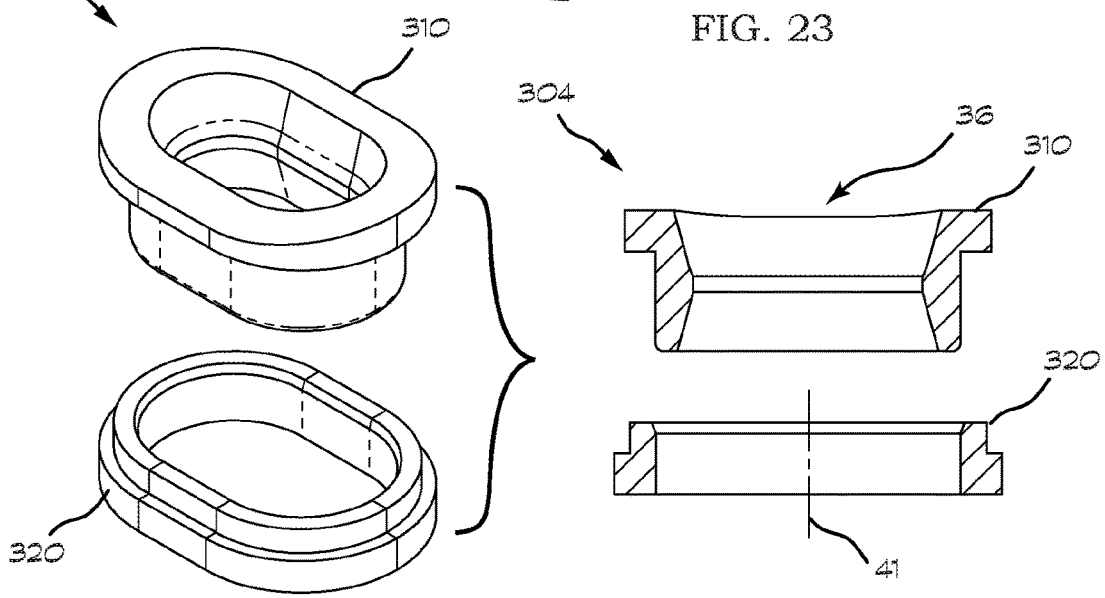
FIG. 24
FIG. 25
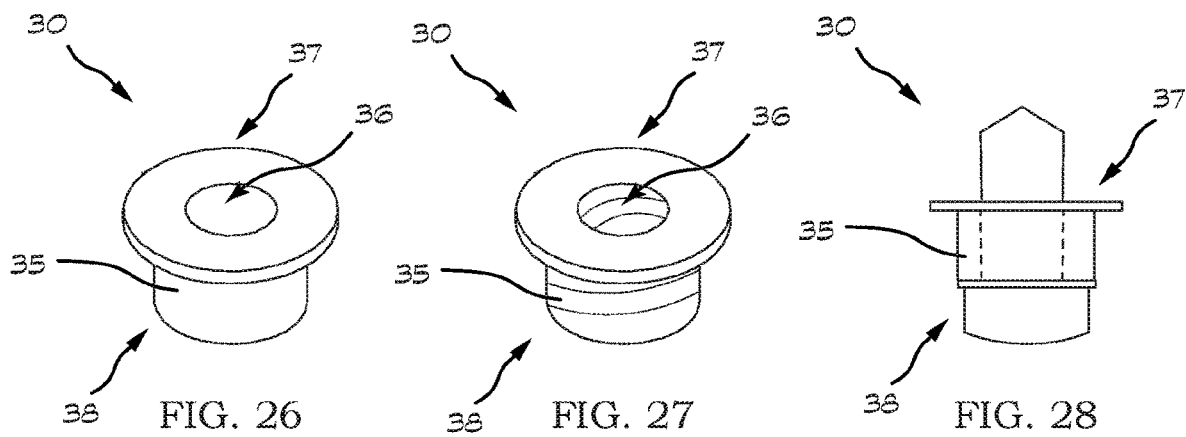
FIG. 26  FIG. 27  FIG. 28

BONE FIXATION SYSTEM

CROSS-REFERENCE TO RELATED APPLICATION

This application is a bypass continuation that claims priority to International Patent Application No. PCT/US22/29159 filed May 13, 2022, which claims priority to U.S. Provisional Patent Application No. 63/188,492 filed May 14, 2021, where the entire content of each of the foregoing is incorporated herein by reference.

TECHNICAL FIELD

The present invention pertains generally to fixation of bone fractures.

BACKGROUND

Bone fractures with multiple fragments, such as a distal radius fracture, are typically fixated with an internal fixation plate and screw device. Some distal radius fracture cases are more severe, and require applying a dorsal spanning fixation plate and screw device. These plates are surgically placed under the skin and tissue on the back of the hand and forearm, and are fixated to the radius at one end and to the second or third metacarpal (top of the hand) at the other end. The plate is fixed to the bone with multiple non-locking or variable angle locking screws. Such a plate holds the fracture fragments "out to length" which is referred to as ligamentotaxis. The secured fracture fragments are held in position for several weeks and then the plate is surgically removed and the subject resumes range of motion activities for the wrist.

Composite, non-metallic, materials present several advantages in bone fixation plating. Materials such as CFR-PEEK (carbon-fiber-reinforced polyetheretherketone) and CFR-PEKK (carbon-fiber-reinforced polyetherketoneketone) have a modulus of elasticity close to that of bone, are radiolucent (i.e., medical imaging can be performed through them), and have a superior tensile strength compared to stainless-steel or titanium.

Some fixation plates made of CFR-PEEK accept titanium-alloy screws which are driven through holes in the composite plate creating a threaded pathway (like a self-tapping screw). However, this threading process may create composite shavings or debris which are undesirable and difficult to remove from the body.

SUMMARY

The embodiments disclosed herein may be summarized as follows.

According to one or more embodiments of a bone fixation system, cooperating with one or more screws for fracture fixation, the one or more screws each having a shank and a threaded body, the system includes:
  a bone fixation plate having a plurality of apertures extending through a thickness of the plate from a top of the plate to a bottom of the plate, each of the plurality of apertures having a generally circular shape or a generally obround shape as viewed from the top of the plate;
  one or more inserts, each insert disposed within one of the plurality of apertures and sized and configured to be closely received thereby, the one or more inserts each having an interior passageway sized to receive one of the one or more screws; and
  wherein the plate is formed of a fiber reinforced polymer composite material and the one or more inserts are formed of a malleable metal.

According to one or more embodiments, the system includes at least one aperture of the plurality of apertures has a generally obround shape as viewed from the top of the plate and is sized and configured to allow longitudinal positioning of one of the one or more screws therein. Embodiments of the disclosure are able to use a non-locking screw in this aperture to allow for adjustment of the position of the plate.

According to one or more embodiments, the system includes each insert being shaped complementary to the aperture wherein the insert is disposed.

According to one or more embodiments, the system includes at least one of the inserts protruding through the bottom of the plate. Embodiments of the disclosure are able to provide clearance between the composite plate and the bone. This arrangement reduces the contact area between the bone and the composite plate, allowing improved vascularity at the fracture site.

According to one or more embodiments, the system includes the interior passageway of at least one of the one or more inserts being sized to receive one of the one or more screws at an angle of between −15 degrees and +15 degrees relative to a lateral axis of the insert.

According to one or more embodiments, the system includes at least one of the one or more inserts including a superior portion and an inferior portion configured to engage the superior portion.

According to one or more embodiments, the system includes the one or more inserts including a keyed surface protrusion and the plurality of apertures each including a groove shaped complementary to the keyed surface protrusion. According to one or more embodiments, the surface protrusion may extend through the thickness of the plate.

According to one or more embodiments, the system includes the one or more inserts including a threaded external surface configured to threadingly engage the aperture wherein the insert is disposed. Embodiments of the disclosure are able to prevent rotation of the insert within the plate when the screws are inserted.

According to one or more embodiments, the disposition of the one or more inserts within the plurality of apertures is configured to resist rotation of the insert relative to the aperture wherein the insert is disposed.

According to one or more embodiments, the one or more screws each having a threaded head, the interior passageway of the one or more inserts is sized and configured such that threadingly inserting the threaded head into the insert deforms a portion of the interior passageway to threadably couple the insert with the threaded head. According to one or more embodiments, self-threading of a portion of the malleable insert significantly reduces the problem of shavings from the composite plate entering the body.

According to one or more embodiments, the plate is formed of carbon-fiber-reinforced polyetheretherketone (CFR-PEEK) or carbon-fiber-reinforced polyetherketoneketone (CFR-PEKK). Embodiments of the disclosure have a modulus of elasticity close to that of bone; and/or are radiolucent.

According to one or more embodiments, the plate has a longitudinally convex shape.

According to one or more embodiments, the plate has two tapered ends having an outwardly decreasing thickness. Embodiments of the disclosure are able to provide ease of insertion under soft tis sue.

According to one or more embodiments, a kit includes a bone fixation plate and one or more inserts in accordance with any of the embodiments disclosed herein.

According to one or more embodiments, a method of fixating a fractured bone includes:
 a) surgically placing the bone fixation system of any of the embodiments disclosed herein adjacent the fractured bone;
 b) passing the one or more screws for fracture fixation through the interior passageway of at least one of the one or more inserts; and
 c) affixing the bone fixation system to the fractured bone with the one or more screws.

Embodiments are provided which are sized, shaped, and configured to accommodate fixation of various bone fractures, including: distal radius fracture; proximal femoral periprosthetic fractures around the femoral hip prosthesis; distal femoral periprosthetic fractures and acute distal femoral fractures; proximal tibial periprosthetic and non-periprosthetic fractures; distal tibial fractures; proximal humerus; volar aspect of the distal radius; dorsal surface of the distal radius, boney surfaces in the distal fibula, hindfoot, mid-foot and forefoot.

These and other aspects of the embodiments will be better appreciated and understood when considered in conjunction with the following description and the accompanying drawings. The following description, while indicating various embodiments and details thereof, is given by way of illustration and not of limitation. Many substitutions, modifications, additions, or rearrangements may be made within the scope of the embodiments, and the embodiments may include all such substitutions, modifications, additions, or rearrangements.

BRIEF DESCRIPTION OF THE DRAWINGS

Non-limiting and non-exhaustive embodiments of the bone fixation system are described with reference to the following figures, wherein like reference numerals refer to like parts throughout the various views unless otherwise specified.

FIG. 17 is a top plan view of an embodiment of a bone fixation plate.

FIG. 18 is a side elevation view of an embodiment of the bone fixation plate.

FIG. 19 is an end view of an embodiment of the bone fixation plate.

FIG. 20 is a cross-sectional view along the line XX-XX of FIG. 18.

FIG. 23 is an enlarged, partial, cross-sectional view of the embodiment of FIG. 21.

FIG. 24 is an enlarged perspective view of an embodiment of an insert.

FIG. 25 is a cross-sectional view of the insert of FIG. 24.

FIG. 26 is an enlarged perspective view of another embodiment of an insert.

FIG. 27 is an enlarged perspective view of another embodiment of an insert.

FIG. 28 is an enlarged perspective view of another embodiment of an insert.

Figure 1:
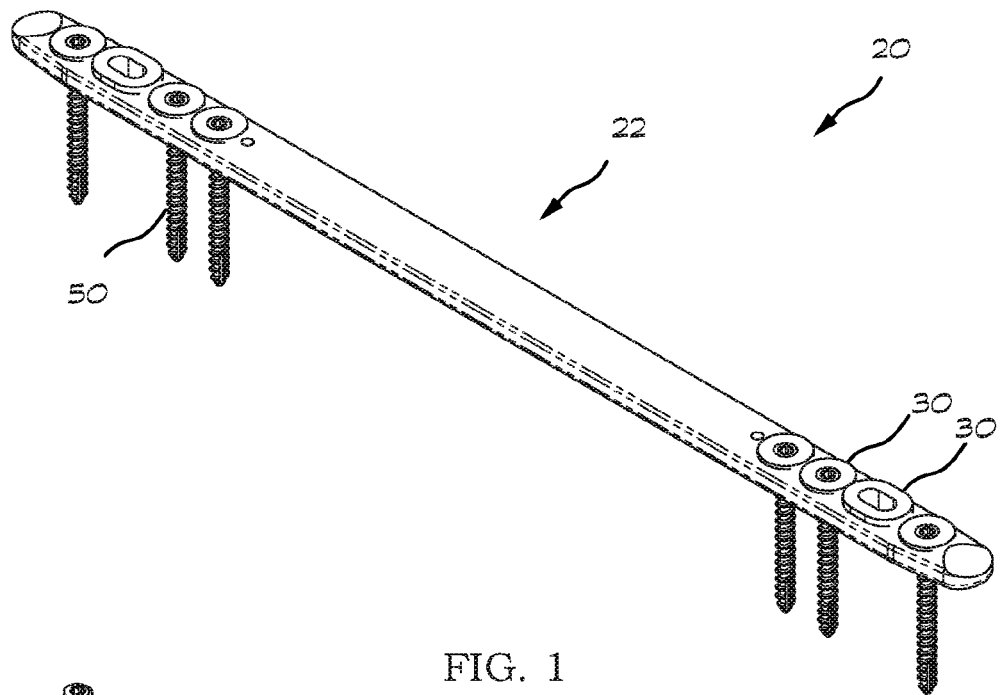
FIG. 1 is a perspective view of an embodiment of a bone fixation system.

Skilled artisans will appreciate that elements in the figures are illustrated for simplicity and clarity and have not necessarily been drawn to scale. For example, the dimensions of some of the elements in the figures may be exaggerated relative to other elements to help improve understanding of various embodiments. Also, common but well-understood elements that are useful or necessary in a commercially feasible embodiment are often not depicted in order to facilitate a less obstructed view of these various embodiments.

LIST OF DRAWING REFERENCE NUMERALS 20 system
22 fixation plate
24 plate end
30 insert
302 cylindrical insert
304 obround insert
310 superior portion
320 inferior portion
35 insert body
36 interior passageway
37 top face
38 bottom face
39 protrusion
40 aperture
402 cylindrical aperture
404 obround aperture
41 lateral axis
46 sidewall
47 upper edge
48 lower edge
49 complementary notch
50 screw
52 threaded body
54 shank 56 head

DETAILED DESCRIPTION

The detailed description describes non-limiting exemplary embodiments. Any individual features may be combined with other features as required by different applications for at least the benefits described herein.

FIGS. 1-4 are perspective, exploded perspective, side elevation, and top plan views, respectively, of an embodiment of a bone fixation system generally designated as 20. The shown embodiment is particularly suitable as a dorsal spanning system for fixation of a distal radius fracture. System 20 includes a bone fixation plate 22 which has a plurality of apertures 40. Each aperture 40 is configured to receive a screw 50 for fracture fixation, which may be a locking or non-locking type of screw.

An insert 30 is disposed within each aperture 40. In embodiments, insert 30 is formed of a malleable metal, such as unalloyed titanium. Each insert has an interior passageway 36 sized to allow passage of a threaded body 52 and a shank 54 of screw 50. Threaded body 52 of the screw is driven into the bone to hold plate 22 in the desired position.

Plate 22 may be formed of a polymer based composite manufactured using a compression molding process, for example, CFR-PEEK (carbon-fiber-reinforced polyetheretherketone) or CFR-PEKK (carbon-fiber-reinforced polyetherketoneketone). Carbon fiber strands may be incorporated in the polymer composite plate to improve mechanical properties. Such materials are advantageous for bone fixation plating as they having a modulus of elasticity close to that of bone, which creates less stress than a comparable titanium alloy or stainless-steel fixation plate. In addition, these composite materials are radiolucent, allowing radiography used during the healing process to image through the plate.

Figure 6:
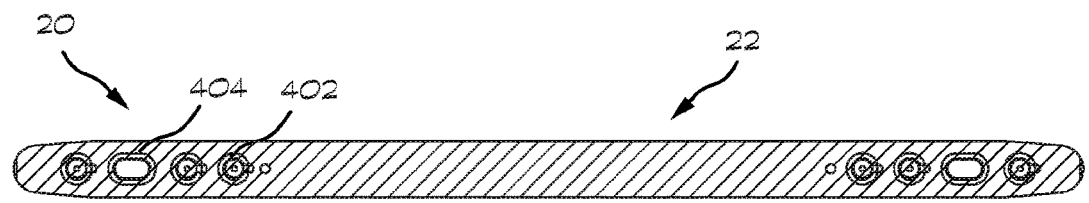
FIG. 6 is a cross-sectional view along the line VI-VI of FIG. 3.

Apertures 40 may have a generally circular or obround shape as viewed from the top of fixation plate 22. Insert 30 may be sized and configured to be closely received by the aperture; for example, the insert may be shaped complementary to the aperture, and/or contact may be made between the insert and the aperture. The embodiment of FIG. 2 includes a cylindrical insert 302 shaped complementary to generally cylindrical aperture 402 and an obround insert 304 shaped complementary to obround aperture 404. These apertures may be seen more clearly in the cross-sectional view of FIG. 6.

As used herein, the term "shaped" means that an item has the overall appearance of a given shape even if there are minor variations from the pure form of said given shape.

As used herein, the terms "generally" or "substantially" when referring to a shape mean that an ordinary observer will perceive that an object has said shape even if there are minor variations from said shape.

As used herein, relative orientation terms, such as "up", "down", "top", "bottom", "left", "right", "vertical", "horizontal", "distal" and "proximal" are defined with respect to an initial presentation of an object and will continue to refer to the same portion of an object even if the object is subsequently presented with an alternative orientation, unless otherwise noted.

As used herein, the conjunction "or" is to be construed inclusively (e.g., "A or B" would be interpreted as "A, or B, or both A and B"; e.g., "A, B, or C" would be interpreted as "A; or B; or C; or any two of A, B, and C; or all three of A, B, and C").

As used in this application with reference to a numerical value, the terms "about", "approximately", or "substantially" refer to a range of values within plus or minus 10% of the specified number.

Figure 5:
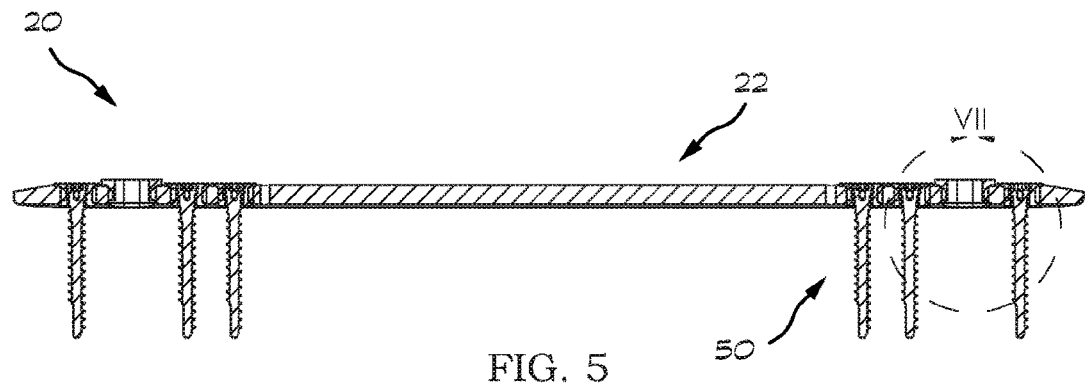
FIG. 5 is a cross-sectional view along the line V-V of FIG. 4.
Figure 7:
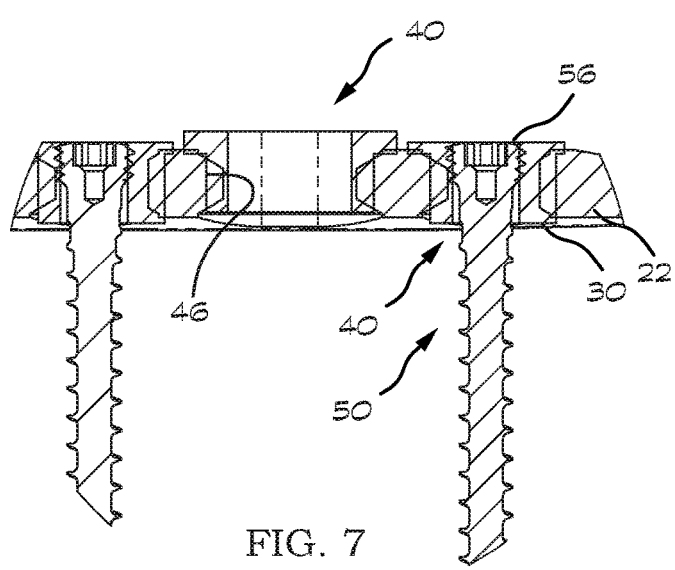
FIG. 7 is an enlarged view of area VII of FIG. 5.

FIG. 5 is a longitudinal cross-sectional view of system 20, and FIG. 7 is an enlarged view of area VII of FIG. 5. Each aperture 40 is defined by a sidewall 46 which extends through the thickness of fixation plate 22 to openings on both the top and bottom of the plate. Insert 30 may contact the entire sidewall of aperture 40; in other words the insert may be configured as a lining for the aperture.

Where head 56 of screw 50 is threaded, as in the case of a locking screw, driving threaded head 56 into insert 30 deforms a portion of interior passageway 36 to threadably couple insert 30 with screw 50 in the region of head 56. The portion of interior passageway 36 not engaged with head 56 will not be deformed and may have smooth walls. In other embodiments, at least a portion of interior passageway may be threaded for engagement with screw 50, prior to engagement with the screw.

In embodiments configured for the head of the screw to deform and couple to the interior passageway, the interior passageway has a diameter smaller than a maximum dimension of the threaded head. The sidewall 46 of aperture 40 is larger than the maximum dimension of the threaded head. In this manner the screw should not contact the sidewall of the aperture, even in self-threading configurations. It is envisioned that an embodiment including a malleable insert sized for self-threading by a screw head will significantly reduce the problem of shavings from the composite fixation plate entering the body.

An embodiment of insert 30 is shown in FIGS. 11-14 in perspective, top plan, side elevation, and end views, respectively. In the shown embodiment, interior passageway 36 has an obround shape. A screw may be positionable along the length of interior passageway 36, which may allow for adjustment of the position of the fixation plate. A non-locking screw may be used in such an insert or when adjustable positioning may be desired.

Figure 2:
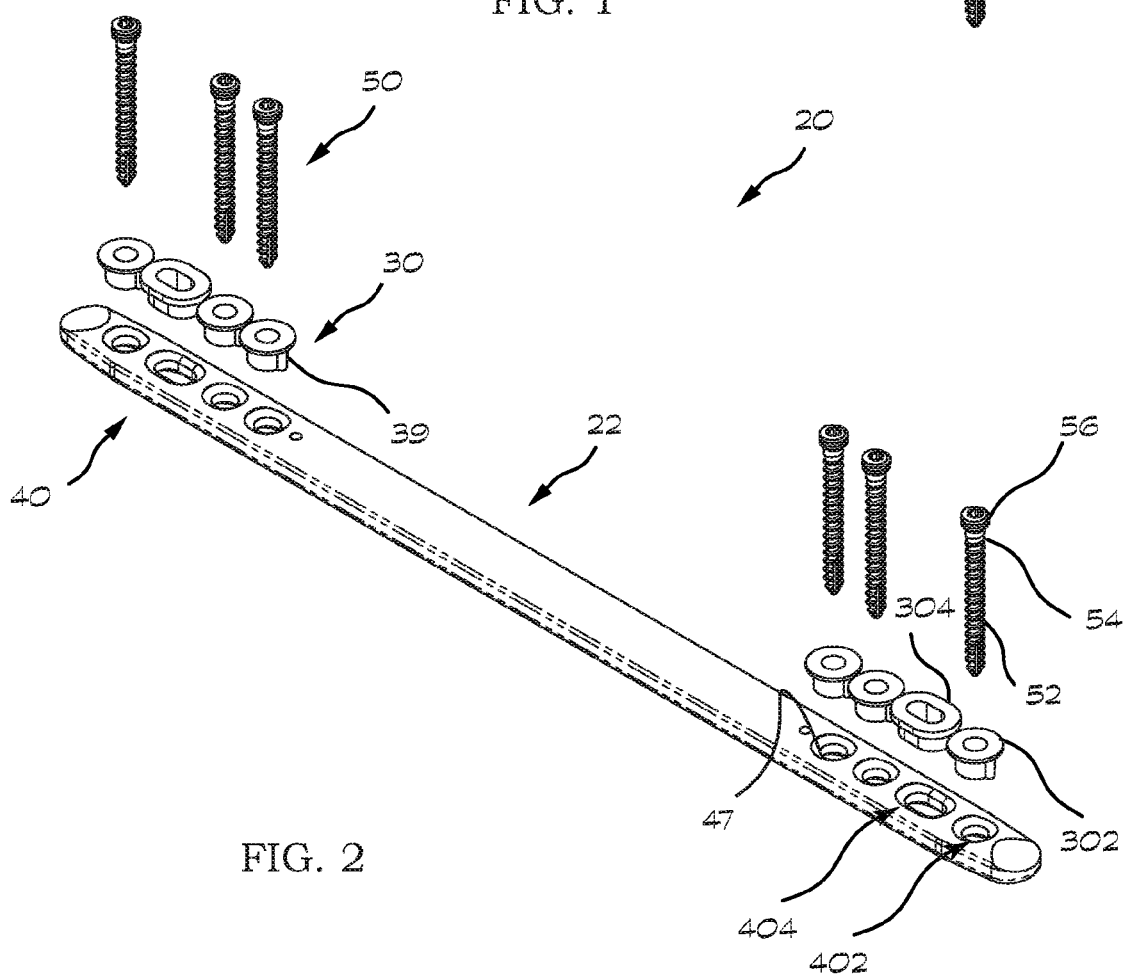
FIG. 2 is an exploded perspective view of an embodiment of the bone fixation system.
Figure 4:
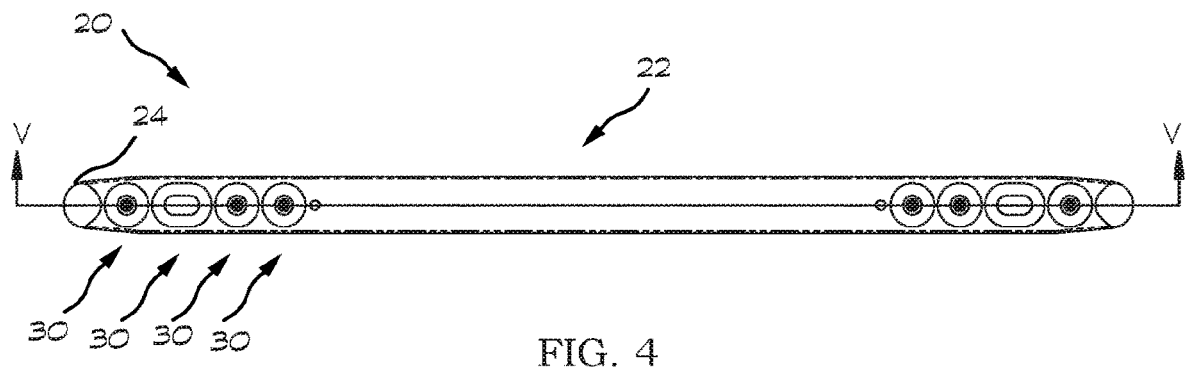
FIG. 4 is a top plan view of an embodiment of the bone fixation system.
Figure 3:
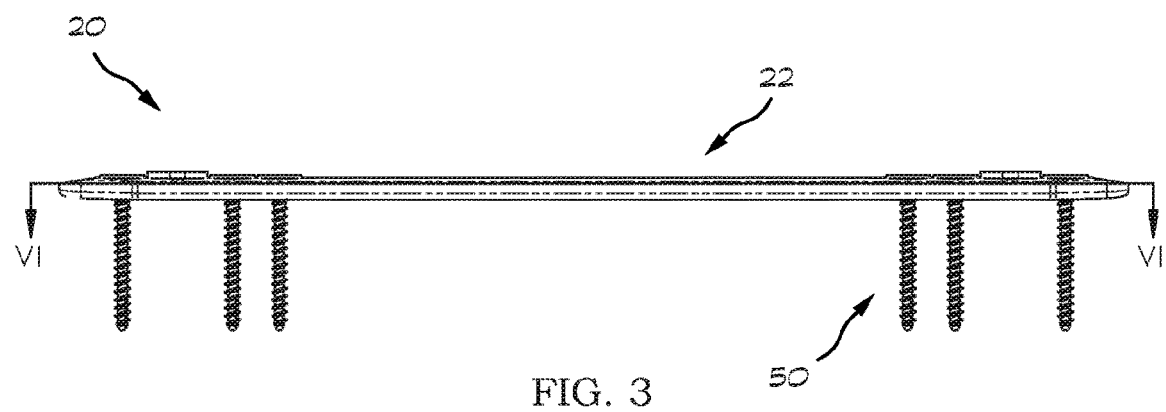
FIG. 3 is a side elevation view of an embodiment of the bone fixation system.

Insert 30 has a top face 37 which may have a circumferential lip extending beyond the outer boundary of insert body 35. As shown in FIGS. 1 & 2, aperture 40 may have a recessed upper edge 47 sized and shaped to fit top face 37 within the recess (see also FIG. 20). This configuration may provide added protection against incidental contact of the screw and plate when the screw is being inserted.

Insert 30 has a bottom face 38 which may similarly be configured with a circumferential lip. An embodiment where the bottom face does not include a lip is shown in FIG. 2. The bottom of plate 22 may include a recessed lower edge 48 of aperture 40, similar to upper edge 47. In another embodiment, an insert with a lip on the bottom face may be disposed in an aperture that does not have a recessed lower edge.

Figure 15:
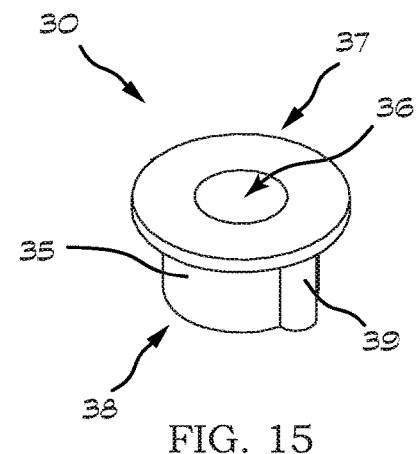
FIG. 15 is an enlarged perspective view of another embodiment of the insert.
Figure 10:
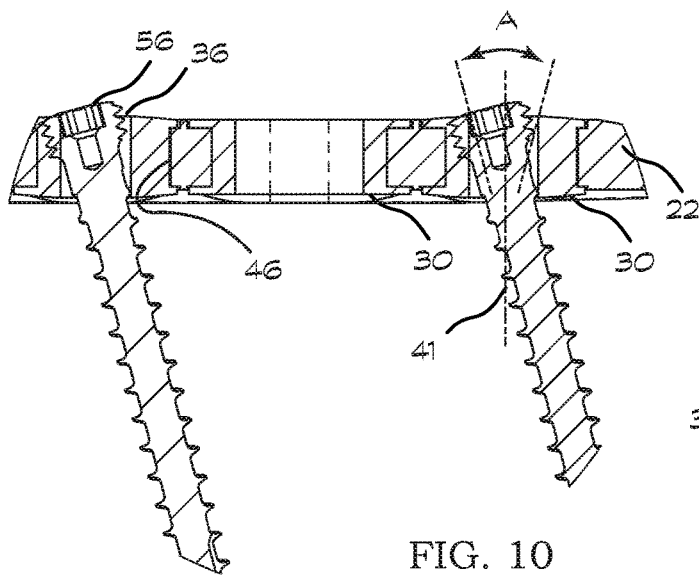
FIG. 10 is an enlarged, partial, cross-sectional view of the embodiment of FIG. 8.
Figure 11:
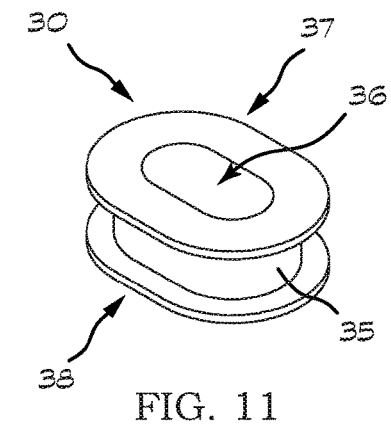
FIG. 11 is an enlarged perspective view of an embodiment of an insert.
Figure 12:
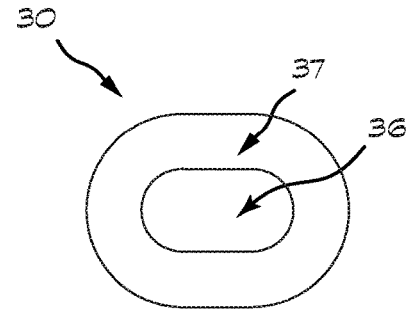
FIG. 12 is a top plan view of the insert of FIG. 11.
Figure 16:
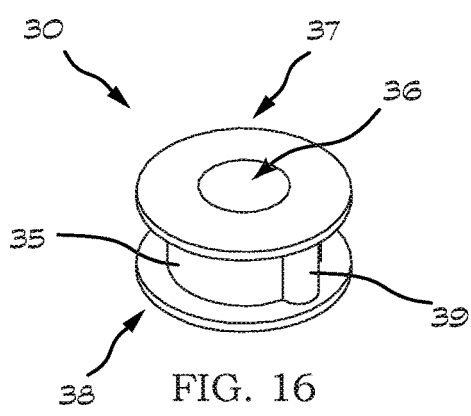
FIG. 16 is an enlarged perspective view of another embodiment of the insert.
Figure 14:
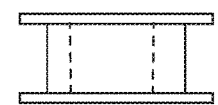
FIG. 14 is an end view of the insert of FIG. 11.
Figure 13:
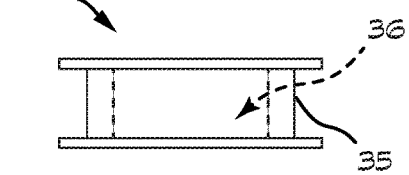
FIG. 13 is a side elevation view of the insert of FIG. 11.

Insert 30 may protrude through plate 22 on the bone side, as shown in FIGS. 7 & 10. In such an arrangement, insert 30 may provide clearance between the fixation plate and the bone, which reduces contact area between the bone and the plate, allowing improved vascularity at the fracture site. In embodiments, some inserts 30 may protrude through plate 22 on the bone side, while other inserts 30 of the same system may not protrude through the plate. In one example case, circular inserts may protrude through the plate, while obround inserts do not protrude through the plate. Additional embodiments of insert 30 are shown in FIGS. 15 & 16. In these embodiments, insert body 35 and interior passageway 36 each have a substantially cylindrical shape. In the FIG.

embodiment, top face 37 has a circumferential lip extending beyond the outer boundary of insert body 35. In the FIG. 16 embodiment, top face 37 and bottom face 38 each have a circumferential lip extending beyond the outer boundary of insert body 35.

Insert body 35 may include a protrusion 39. Protrusion 39 is configured for location within a complementary notch 49 in the fixation plate (see FIG. 20). This feature may prevent rotation of the insert within the fixation plate when a screw is coupled to the insert. Protrusion 39 and complementary notch 49 of the shown embodiments extend through the entire thickness of fixation plate 22. In alternate embodiments, the protrusion and complementary notch may extend through a partial thickness of the fixation plate. While protrusion 39 is shown to have a columnar shape, other shapes may be readily envisioned to achieve an equivalent result, such as spherical segment, a keystone shape, or a chevron shape.

Embodiments of insert 30 may be unitarily formed or may include multiple pieces. Insert 30 may be assembled to fixation plate 22 such that the insert is retained by the fixation plate. For example, insert 30 may be installed like a rivet, may have top and bottom parts lockingly engaged together, or may be press fit into the plate.

Figure 8:
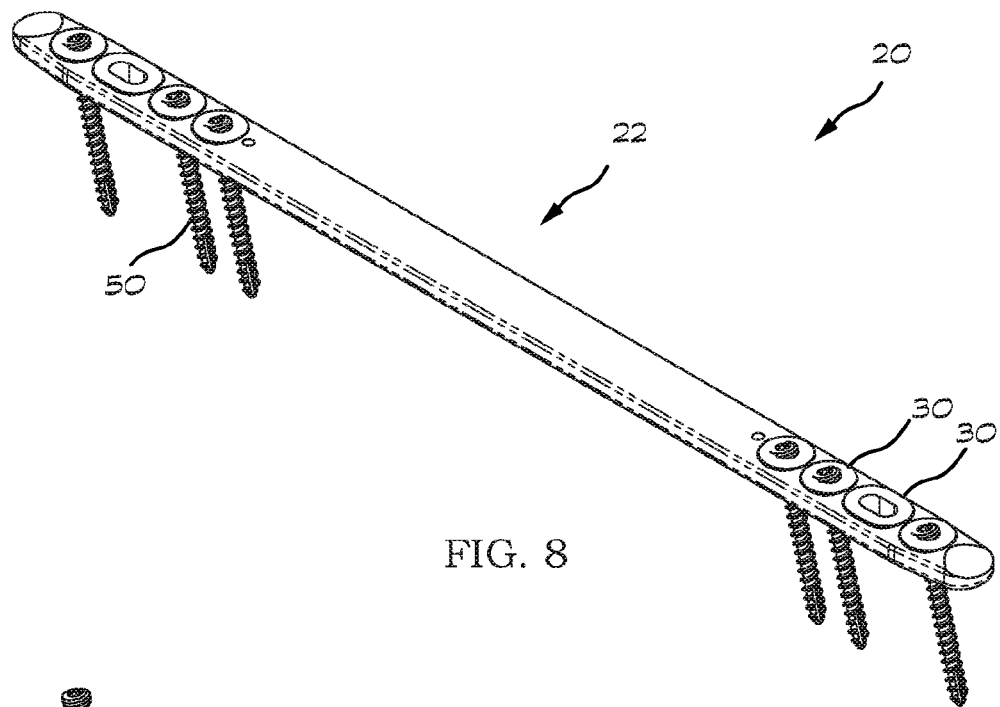
FIG. 8 is a perspective view of another embodiment of the bone fixation system.
Figure 9:
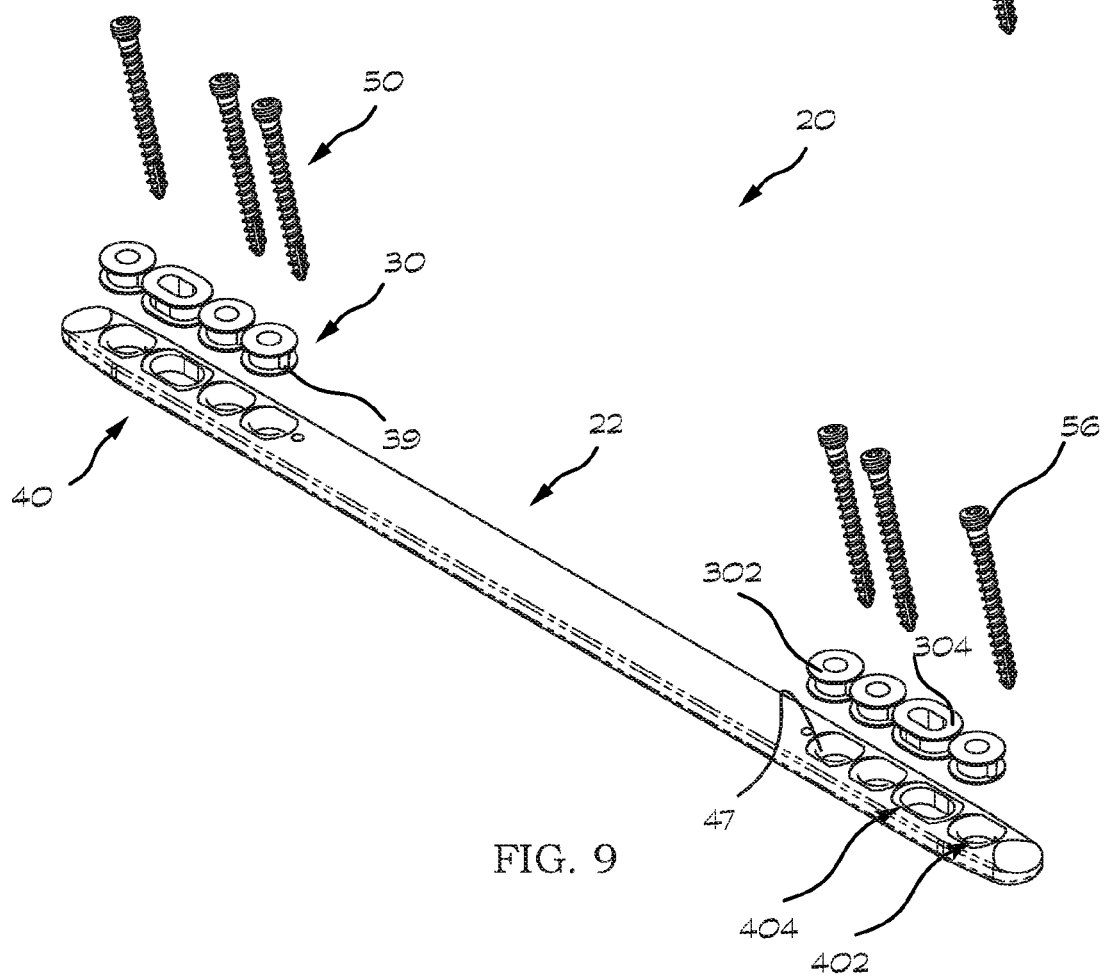
FIG. 9 is an exploded perspective view of the embodiment of FIG. 8.

FIGS. 8-10 illustrate another embodiment of the bone fixation system. Interior passageways 36 are sized to provide sufficient clearance for insertion of screws 50 through the passageway over a range of angles, A, relative to a lateral axis 41 of the aperture. In embodiments, screw 50 may be inserted over a range of angles of between about −15 degrees and +15 degrees.

FIG. 17-19 are top plan, side elevation, and end views, respectively of an embodiment of fixation plate 22. FIG. 20 is a cross-sectional view along the line XX-XX of FIG. 18. In the shown embodiment, fixation plate 22 includes both substantially cylindrical apertures and substantially obround apertures. Plate ends 24 of fixation plate 22 may be tapered (e.g., at an angle α) to ease insertion of the plate under soft tissue. In embodiments, fixation plate 22 may have a longitudinally convex shape, as best seen in FIG. 19. This shape may increase the strength of the fixation plate.

Figure 21:
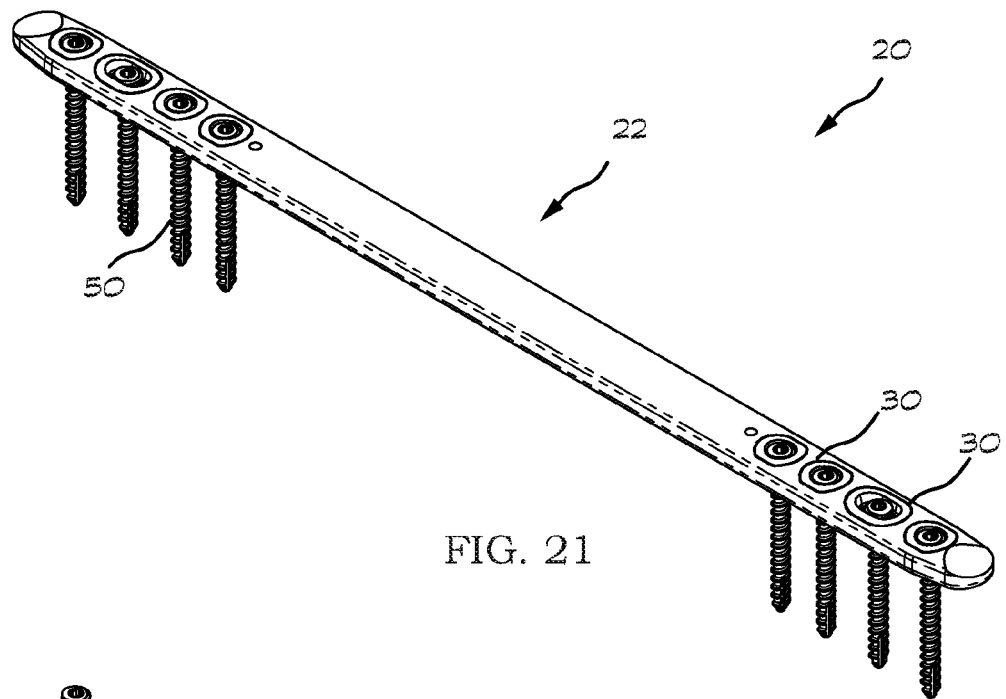
FIG. 21 is a perspective view of another embodiment of the bone fixation system.
Figure 22:
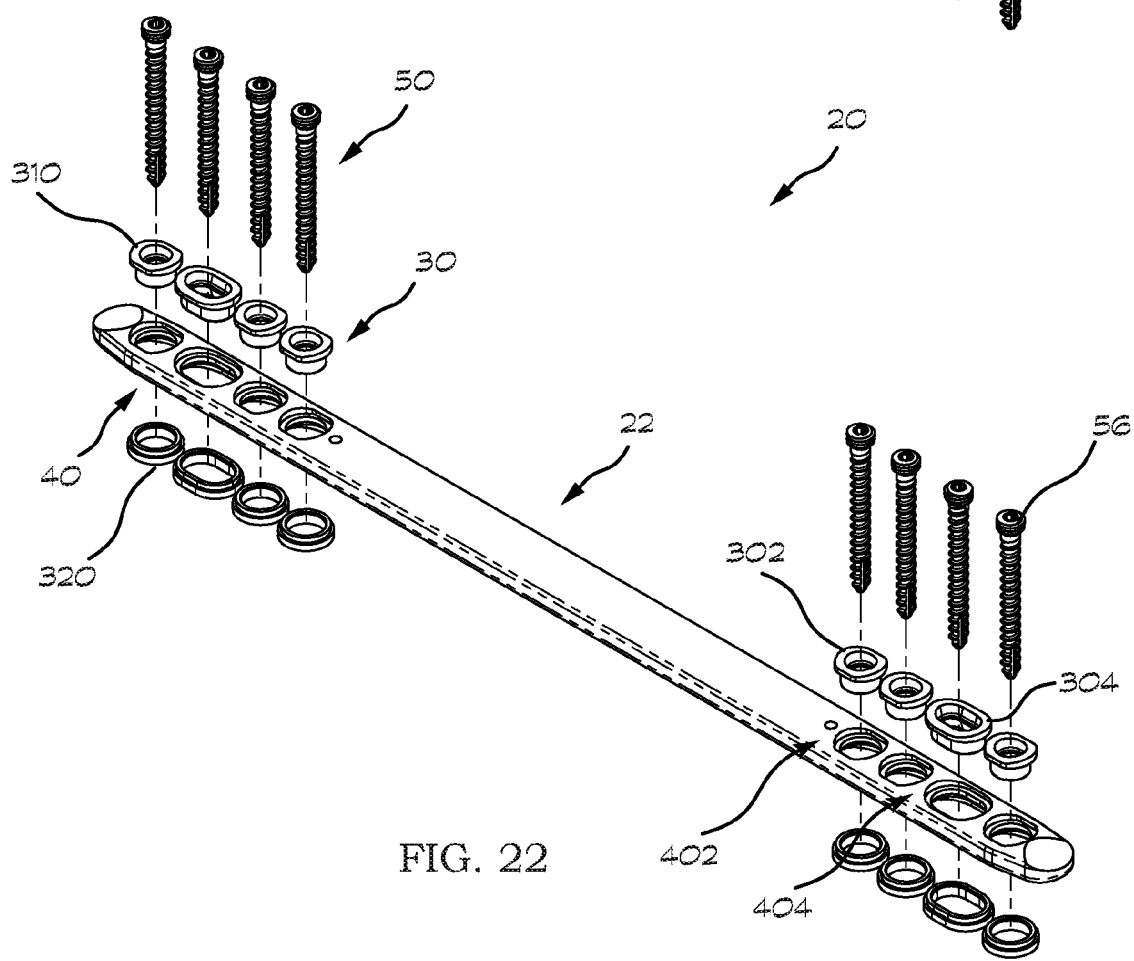
FIG. 22 is an exploded perspective view of the embodiment of FIG. 21.

FIGS. 21-23 are, respectively, perspective, exploded perspective, and enlarged, partial, cross-sectional views of another embodiment of bone fixation system 20. In this embodiment, system 20 includes six of cylindrical aperture 402 and two of obround aperture 404. Each insert 30 disposed within one of the apertures includes a superior portion 310 and an inferior portion 320. Inferior portion 320 is configured to engage the superior portion 310, as shown in FIG. 23. For example, inferior portion 320 and superior portion 310 may be press-fit together, may be lockingly engaged, may be threadably engaged, or may be engaged by other means. In some aspects, the engagement between inferior portion 320 and superior portion 310 may be configured to resist rotation of insert 30 relative to aperture 40 in which the particular insert is disposed.

FIGS. 24-25 are enlarged perspective and cross-sectional views, respectively, of an embodiment of an insert, e.g. an obround insert 304. The shown insert 304 includes a superior portion 310 and an inferior portion 320 configured to engage the superior portion. Interior passageway 36 of insert 304 is sized and shaped to allow clearance for insertion of a screw through passageway 36 over a range of angles relative to lateral axis 41 of the aperture. While all of the inserts shown in this embodiment include a superior portion and an inferior portion, this need not be the case. In a given system, one or more inserts may include a superior portion and an inferior portion while other inserts of the same system do not.

FIG. 26 is an enlarged perspective view of another embodiment of insert 30. In this embodiment, insert body 35 is generally smooth and has a substantially cylindrical shape. Top face 37 has a circumferential lip extending beyond the outer boundary of insert body 35. Insert 30 may, or may not, be sized such that bottom face 38 protrudes through the bottom of the plate.

FIG. 27 is an enlarged perspective view of another embodiment of insert 30, wherein insert body 35 has a substantially cylindrical shape. In this embodiment, either one or both of insert body and interior passageway 36 may be threaded (both are shown threaded here). Providing threads on insert body 35 (i.e., external threads) may enable the insert to threadingly engage an aperture of the plate. Such engagement resists rotation of the insert within the aperture, e.g., when a screw is driven into the insert. Similarly interior passageway 36 may be threaded (i.e., internal threads) for engagement with a screw. Interior passageway 36 may be machine threaded prior to insertion of the screw, or may be sufficiently malleable that driving a screw into the interior passageway forms threads in the interior passageway. It is envisioned that driving a screw into an insert formed of sufficiently soft material (e.g., commercially pure (CP) titanium grade 1 or 2) would deform the insert without creating particulate debris.

FIG. 28 is an enlarged perspective view of another embodiment of insert 30, wherein insert body 35 has a substantially cylindrical shape. Insert 30 of the shown embodiment is generally shaped like a blind rivet and may be inserted into a plate in a similar manner. Top face 37 may have a circumferential lip extending beyond the outer boundary of insert body 35 and configured to surround a top surface of an aperture of the fixation plate. Bottom face 38 may protrude through the bottom of the plate and be deformed in the rivet-style insertion process to form a lip around a bottom surface of the aperture.

In some embodiments, interior passageways 36 may be sized to provide clearance for a drill sleeve instrument for drilling a pilot hole in the bone prior to insertion of the screw.

Additional exemplary embodiments are provided below.
System for Proximal Femoral Periprosthetic Fracture A composite, non-metallic plate with metal inserts that accept locking or non-locking screws may be configured for use in fixation of proximal femoral periprosthetic fractures around the femoral hip prosthesis. The plate may have a hook configuration that attaches proximally to the greater trochanter of the femur. The plate is configured to extend distally down the lateral shaft of the femur past the tip of the hip prosthesis and the fracture site and be secured with unicortical and bicortical locking and non-locking screws. The plate may have grooves along its length to accept metallic bone cables for additional bone fixation.
System for Distal Femoral Fracture A composite, non-metallic plate with metal inserts that accepts locking and non-locking screws may be configured for use in fixation of distal femoral periprosthetic fractures and acute distal femoral fractures. The plate may be attached to an external outrigger device for insertion of the plate and act as an aiming arm for the percutaneous placement of locking and non-locking screws from the lateral aspect of the femur. The distal end of the plate may accept multiple locking and non-locking screws at predetermined angles by the aiming arm within the distal condyle of the femur. The femoral shaft may accept multiple locking or non-locking bicortical and unicortical screws through the external aiming arm extending proximally along the shaft past the fracture site for secure fixation.

System for Proximal Tibial Fracture

A composite, non-metallic plate with metal inserts that accepts locking and non-locking screws may be configured for use in fixation of proximal tibial periprosthetic and non-periprosthetic fractures. The proximal portion of the plate may have predetermined angles for the screws through an external outrigger device and accept multiple locking and non-locking bicortical and unicortical screws within the entire tibial plateau. The plate may be configured to extend distally past the fracture site and accept multiple percutaneous locking and non-locking shaft screws through the external outrigger device along the lateral shaft of the tibia.

System for Distal Tibial Fracture

A composite, non-metallic plate with metal inserts that accepts non-locking and locking screws may be configured for use in fixation of distal tibial fractures. The distal end of the plate may be attached to an external outrigger device on the lateral aspect of the tibia and have predetermined angles for the multiple insertion of bicortical locking and non-locking screws within the tibial plafond as well as for percutaneous insertion of the plate. The plate may extend proximally along the shaft of the tibia past the fracture site and accept locking and non-locking screws percutaneously through the external outrigger device.

System for Proximal Humerus Fracture

A composite, non-metallic plate with metal inserts that accepts locking and non-locking screws may be configured for use in fixation of the proximal humerus. The proximal portion of the plate may be attached to an external outrigger device and placed on the lateral aspect of the humerus by inserting it percutaneously and may have predetermined screw angles for the placement of multiple locking and non-locking screws within the proximal head of the humerus. The plate may extend distally past the fracture site and locking and non-locking shaft screws may be placed through the external outrigger device percutaneously along the lateral aspect of the humerus.

System for Fractures of the Volar Aspect of the Distal Radius

A composite, non-metallic plate with metal inserts that accepts locking and non-locking screws may be configured for use in fixation of fractures of the volar aspect of the distal radius. The plate may have multiple locking and non-locking options in a T-shaped configuration covering the distal footprint of the three columns of the distal radius. The plate may accept a drill sleeve and drill for predetermined angles. The screws may be inserted through a guide that also accepts the drill sleeve. The plate may be configured to extend proximally past the fracture site and accept multiple locking or non-locking screws along the distal radius volar shaft.

System for Fractures of the Dorsal Surface of the Distal Radius

A composite, non-metallic plate with metal inserts that accepts locking and/or non-locking screws may be configured for use in fixation of multiple fractures of the dorsal surface of the distal radius. A series of fragment specific plates designed for the lateral, medial, and intermediate columns, as well as the lateral aspect of the distal radius to capture fracture fragments that cannot be reduced and fixated by distal radius volar plating alone.

Further embodiments are envisioned for fixation of boney surfaces in the distal fibula, hind-foot, mid-foot, and fore-foot.

Further envisioned is a kit including a bone fixation system according to any of the embodiments described above and including a plurality of screws for affixing the plate to bone. The screws may be locking or non-locking screws.

In the present disclosure, the verb "may" is used to designate optionality/non-compulsoriness. In other words, something that "may" can, but need not. In the present disclosure, the verb "comprise" may be understood in the sense of including. Accordingly, the verb "comprise" does not exclude the presence of other elements/actions. In the present disclosure, relational terms such as "first," "second," "top," "bottom" and the like may be used solely to distinguish one entity or action from another entity or action without necessarily requiring or implying any actual such relationship or order between such entities or actions.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

In the present disclosure, expressions in parentheses may be understood as being optional. As used in the present disclosure, quotation marks may emphasize that the expression in quotation marks may also be understood in a figurative sense. As used in the present disclosure, quotation marks may identify a particular expression under discussion.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of the invention, even those disclosed solely in combination with other features of the invention, may be combined in any configuration excepting those readily apparent to the person skilled in the art as nonsensical. Likewise, use of the singular and plural is solely for the sake of illustration and is not to be interpreted as limiting.

The invention claimed is:

1. A bone fixation system, cooperating with one or more screws for fracture fixation, the one or more screws each having a shank, a threaded head, and a threaded body, the system comprising:
   a bone fixation plate having a plurality of apertures extending through a thickness of the plate from a top of the plate to a bottom of the plate, each of the plurality of apertures being defined by a sidewall extending through the thickness, each of the plurality of apertures having a generally circular shape or a generally obround shape as viewed from the top of the plate;
   at least one aperture of the plurality of apertures having a generally obround shape as viewed from the top of the plate and being sized and configured to allow longitudinal positioning of one of the one or more screws therein;
   one or more inserts, each insert disposed within one of the plurality of apertures and sized and configured to be closely received thereby, the one or more inserts each having an interior passageway sized to receive one of the one or more screws;

an obround insert shaped complementary to the at least one aperture having a generally obround shape and disposed therein such that the obround insert contacts the entire sidewall of the at least one aperture;

wherein the interior passageway of the one or more inserts is sized and configured such that threadingly inserting the threaded head into the insert deforms a portion of the interior passageway to threadably couple the insert with the threaded head; and wherein the plate is formed of a fiber reinforced polymer composite material and the one or more inserts are formed of a malleable metal.

2. The bone fixation system of claim 1, wherein each insert is shaped complementary to the aperture wherein the insert is disposed.

3. The bone fixation system of claim 1, wherein at least one of the one or more inserts protrudes through the bottom of the plate.

4. The bone fixation system of claim 1, wherein the interior passageway of at least one of the one or more inserts is sized to receive one of the one or more screws at an angle of between −15 degrees and +15 degrees relative to a lateral axis of the insert.

5. The bone fixation system of claim 1, wherein at least one of the one or more inserts includes a superior portion and an inferior portion configured to engage the superior portion.

6. A bone fixation system, cooperating with one or more screws for fracture fixation, the one or more screws each having a shank and a threaded body, the system comprising:
a bone fixation plate having a plurality of apertures extending through a thickness of the plate from a top of the plate to a bottom of the plate, each of the plurality of apertures being defined by a sidewall extending through the thickness, each of the plurality of apertures having a generally circular shape or a generally obround shape as viewed from the top of the plate;
at least one aperture of the plurality of apertures having a generally obround shape as viewed from the top of the plate and being sized and configured to allow longitudinal positioning of one of the one or more screws therein;
one or more inserts, each insert disposed within one of the plurality of apertures and sized and configured to be closely received thereby, the one or more inserts each having an interior passageway sized to receive one of the one or more screws;
an obround insert shaped complementary to the at least one aperture having a generally obround shape and disposed therein such that the obround insert contacts the entire sidewall of the at least one aperture;
wherein the plate is formed of a fiber reinforced polymer composite material and the one or more inserts are formed of a malleable metal; and
wherein the one or more inserts include a keyed surface protrusion and the plurality of apertures each include a groove shaped complementary to the keyed surface protrusion.

7. The bone fixation system of claim 1, wherein the disposition of the one or more inserts within the plurality of apertures is configured to resist rotation of the insert relative to the aperture wherein the insert is disposed.

8. The bone fixation system of claim 1, wherein the plate is formed of carbon-fiber-reinforced polyetheretherketone (CFR-PEEK) or carbon-fiber-reinforced polyetherketoneketone (CFR-PEKK).

9. The bone fixation system of claim 1, wherein the plate has a longitudinally convex shape.

10. The bone fixation system of claim 1, wherein the plate has two tapered ends having an outwardly decreasing thickness.

11. A bone fixation kit comprising:
a bone fixation plate having a plurality of apertures extending through a thickness of the plate from a top of the plate to a bottom of the plate, each of the plurality of apertures being defined by a sidewall extending through the thickness, each of the plurality of apertures having a generally circular shape or a generally obround shape as viewed from the top of the plate;
one or more screws for fracture fixation, the one or more screws each having a shank, a threaded head, and a threaded body;
at least one aperture of the plurality of apertures having a generally obround shape as viewed from the top of the plate and being sized and configured to allow longitudinal positioning of one of the one or more screws therein;
one or more inserts, each insert configured for disposition within one of the plurality of apertures and sized and configured to be closely received thereby, the one or more inserts each having an interior passageway sized to receive one of the one or more screws;
an obround insert shaped complementary to the at least one aperture having a generally obround shape and configured for disposition therein such that the obround insert contacts the entire sidewall of the at least one aperture;
wherein the interior passageway of the one or more inserts is sized and configured such that threadingly inserting the threaded head into the insert deforms a portion of the interior passageway to threadably couple the insert with the threaded head; and
wherein the plate is formed of a fiber reinforced polymer composite material and the one or more inserts are formed of a malleable metal.

12. A method of fixating a fractured bone, the method comprising:
a) surgically placing a bone fixation system adjacent the fractured bone, the bone fixation system cooperating with one or more screws for fracture fixation, the one or more screws each having a threaded head, the bone fixation system including:
a bone fixation plate having a plurality of apertures extending through a thickness of the plate from a top of the plate to a bottom of the plate, each of the plurality of apertures being defined by a sidewall extending through the thickness, each of the plurality of apertures having a generally circular shape or a generally obround shape as viewed from the top of the plate;
at least one aperture of the plurality of apertures having a generally obround shape as viewed from the top of the plate and being sized and configured to allow longitudinal positioning of one of the one or more screws therein;
one or more inserts, each insert disposed within one of the plurality of apertures and sized and configured to be closely received thereby, the one or more inserts each having an interior passageway sized to receive one of the one or more screws;
an obround insert shaped complementary to the at least one aperture having a generally obround shape and disposed therein such that the obround insert contacts the entire sidewall of the at least one aperture;

wherein the interior passageway of the one or more inserts is sized and configured such that threadingly inserting the threaded head into the insert deforms a portion of the interior passageway to threadably couple the insert with the threaded head; and wherein the plate is formed of a fiber reinforced polymer composite material and the one or more inserts are formed of a malleable metal;

b) passing one or more screws for fracture fixation through the interior passageway of at least one of the one or more inserts; and c) affixing the bone fixation system to the fractured bone with the one or more screws.

\* \* \* \* \*